United States Patent
Domangue et al.

(12)

(10) Patent No.: US 9,414,952 B2
(45) Date of Patent: Aug. 16, 2016

(54) DEVICE FOR TREATING HALLUX VARUS

(75) Inventors: Todd Domangue, Woodstock, GA (US); Russell L. Vedeloff, Greensboro, MD (US)

(73) Assignee: DYNASPLINT SYSTEMS, INC., Severna Park, MD (US)

(*) Notice: Subject to any disclaimer, the term of this patent is extended or adjusted under 35 U.S.C. 154(b) by 703 days.

(21) Appl. No.: 12/587,374

(22) Filed: Oct. 6, 2009

(65) Prior Publication Data
US 2011/0082405 A1 Apr. 7, 2011

(51) Int. Cl.
*A61F 5/00* (2006.01)
*A61F 5/01* (2006.01)

(52) U.S. Cl.
CPC ..................... *A61F 5/019* (2013.01)

(58) Field of Classification Search
CPC ..... A61F 5/019; A61F 5/05875; A61F 5/058; A61F 5/10; A61F 5/11
USPC ........... 128/882, 893, 894; 602/2, 13, 14, 30, 602/60, 61, 62, 22, 322; 607/96, 108, 109, 607/110, 111, 112, 5, 13, 2; 2/21
See application file for complete search history.

(56) References Cited

U.S. PATENT DOCUMENTS

| | | | | |
|---|---|---|---|---|
| 2,016,930 A | * | 10/1935 | McCahan et al. | 601/27 |
| 2,150,645 A | * | 3/1939 | Carroll et al. | 602/30 |
| 2,359,023 A | * | 9/1944 | Danner | 601/46 |
| 2,492,312 A | * | 12/1949 | Muller | 602/30 |
| 4,244,359 A | * | 1/1981 | Dieterich | 602/30 |
| 2005/0187506 A1 | * | 8/2005 | Reinhardt | 602/30 |

* cited by examiner

*Primary Examiner* — Kim M Lewis
(74) *Attorney, Agent, or Firm* — Hauptman Ham, LLP

(57) ABSTRACT

A device for straightening a toe which has deviated away from a midline of a foot includes an assembly for retaining the toe, a tension mechanism and an assembly for securely positioning the foot in the device, such that when pressure is applied to the toe, the toe can be returned to its normal position. The tension mechanism is able to produce a graded amount of tension.

20 Claims, 11 Drawing Sheets

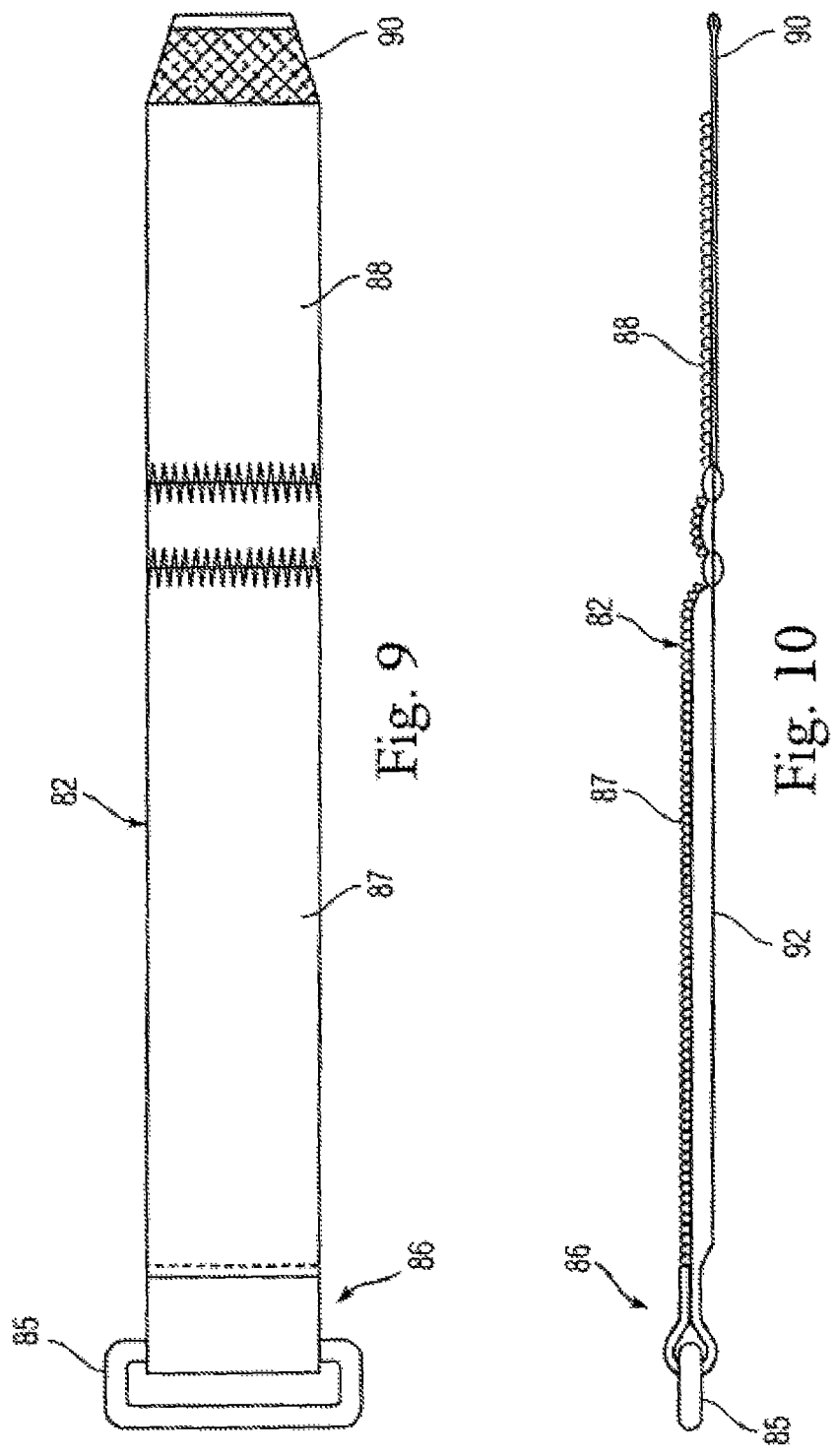

DEVICE FOR TREATING HALLUX VARUS

FIELD OF THE INVENTION

The herein disclosed invention is directed to the orthopedic treatment of the foot.

BACKGROUND OF THE INVENTION

Hallux varus is a condition in which the big toe begins to deviate away from the midline of the foot. In this condition there is a deformity of the great toe joint where the hallux is deviated medially (towards the midline of the body) away from the first metatarsal. Hallux Varus has variable degrees of severity, symptomatology, and etiology. Causes range from the most common iatrogenic postoperative variety of idiopathic, rheumatic, and post traumatic (tear of the hallux lateral collateral ligament). Flexible hallux varus is a common finding in newborn children and usually corrects in early childhood when walking begins.

A few reports exist of traumatic hallux varus following sports injuries. Of these cases, hallux varus occurred secondary to rupture of the lateral collateral ligament and conjoined tendon.

BRIEF SUMMARY OF THE INVENTION

The invention is directed to a passive therapy device wherein graded pressure is placed on a misdirected toe to help the toe to return to its normal position.

OBJECT OF THE INVENTION

A main object of the invention is to produce a device which will aid in returning a misdirected toe to its normal position.

A further object is to produce a device which will hasten the toe's return to normal.

These and other objects of the present invention will become apparent from a reading of the following specification taken in conjunction with the enclosed drawings.

BRIEF DESCRIPTION OF THE DRAWINGS

FIG. 9 is a top plan view of the toe cuff.

FIG. 10 is a side plan view thereof.

DESCRIPTION OF THE INVENTION

Device for Treating Hallux Varus

Figure 1:
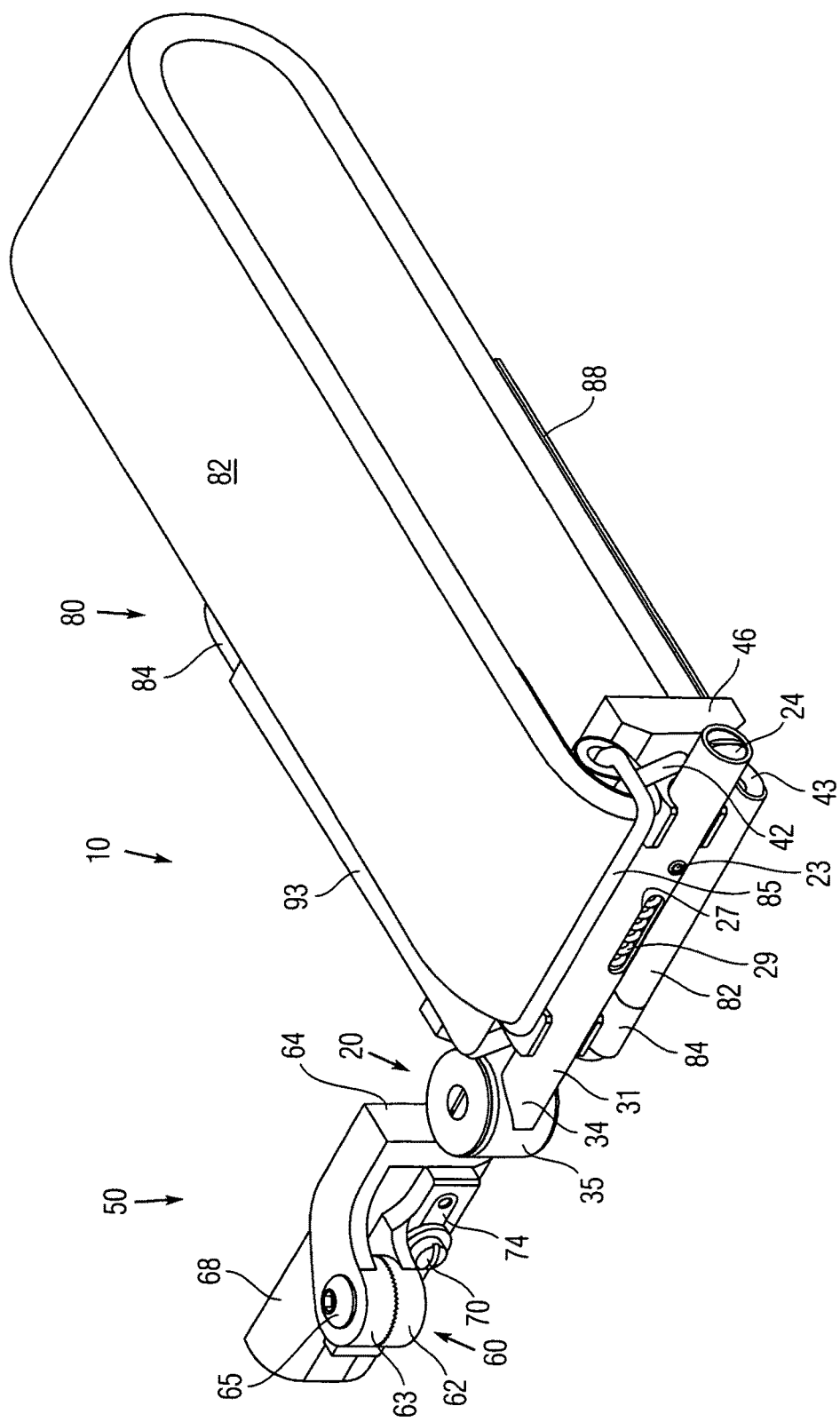
FIG. 1 is a top perspective view of the inventive device for treating hallux varus. Part of the toe cradle has been cut away for ease of illustration.

In the drawings there is shown the Device for Treating Hallux Varus 10 of this invention. With particular attention to FIGS. 1, 2, and 3 there is shown views of the Device for Treating Hallux Varus 10. The device or unit can be identified as having three main components, namely a tension mechanism assembly 20, the toe cradle assembly 50 and a foot positioning assembly 80. The Hallux Varus Unit FIG. 1 has a top position for treating the right toe and can be turned over for the bottom position to treat the left toe. That is the top and bottom of the unit are mirror images of each other.

The device for treating Hallux Varus 10 is a passive therapy device. That is, the device once it is set applies pressure to the misdirected toe passively at a constant rate with the intent that this pressure applied to the misdirected toe will bring the toe back to its normal position and, as required, the pressure can be increased (as will be explained).

The device itself is of rather modest dimensions, fitting over the arch of the foot and abutting the misdirected toe, as will be further explained.

Toe Cradle Assembly

Figure 2:
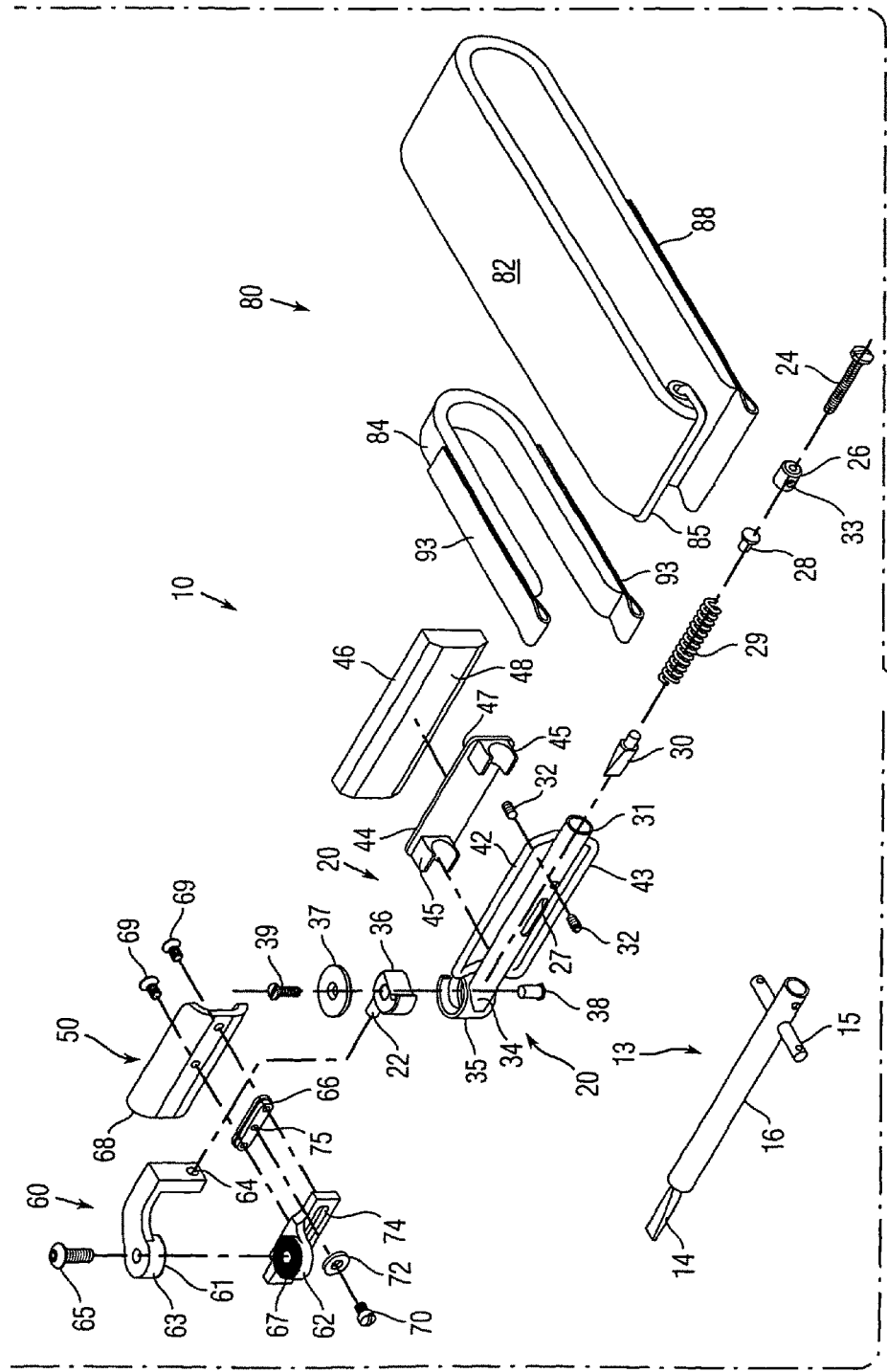
FIG. 2 is an exploded view thereof. The toe cradle is shown.

Referring to FIG. 2, the toe cradle assembly 50 also has a pivot mechanism 60 comprised of a toe cradle base pivot housing 62 (bottom portion) and a stem rod pivot adapter 64 attached to toe cradle base pivot top member 63. In addition, the toe cradle assembly 50 is comprised of a toe cradle base 66 and toe cradle 68, which toe cradle 68 retains the toe during therapy. The toe cradle assembly 50 is assembled by attaching the toe cradle 68 to the toe cradle base 66 employing two toe cradle screws 69. The toe cradle base pivot housing 62 is attached to the toe cradle base 66 using a toe cradle locking screw 70, and a toe cradle locking screw washer 72, wherein the toe cradle locking screw 70, projects through slot 74 in the base of the toe cradle base pivot housing 62 to attach in a tapped hole 75 in the toe cradle base 66.

With particular attention to FIGS. 2 and 4-7, the toe cradle base pivot housing top member 63 fits on toe cradle base pivot housing 62 and is held in place with pivot screw 65. Note particularly that pivot housing 62 and pivot housing top member 63 are held securely in place by teeth 61 and 67 which engage to hold pivot housing top members 63 to the bottom cradle base pivot housing 62; the function of which will be explained below.

Note particularly FIG. 2 that stem rod pivot adapter 64 (female) is engaged by stem rod 22 (male) to join the toe cradle assembly 50 to the tension mechanism assembly 20 in order to apply pressure to the toe in order to straighten the toe from its bent position.

Tension Mechanism

Figure 13:
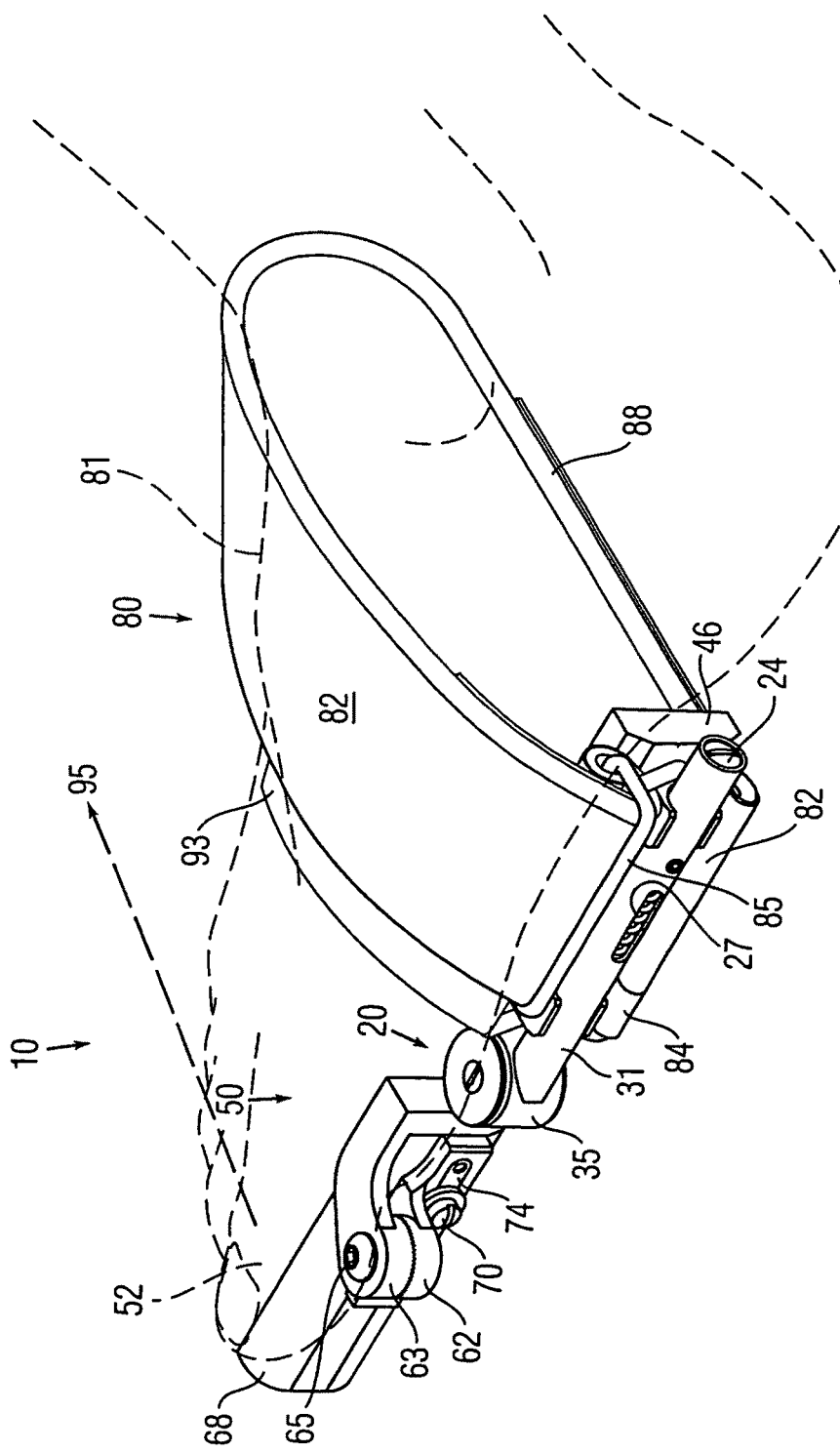
FIG. 13 is a view showing the foot and toe positioned in the device for treating hallux varus.
Figure 14:
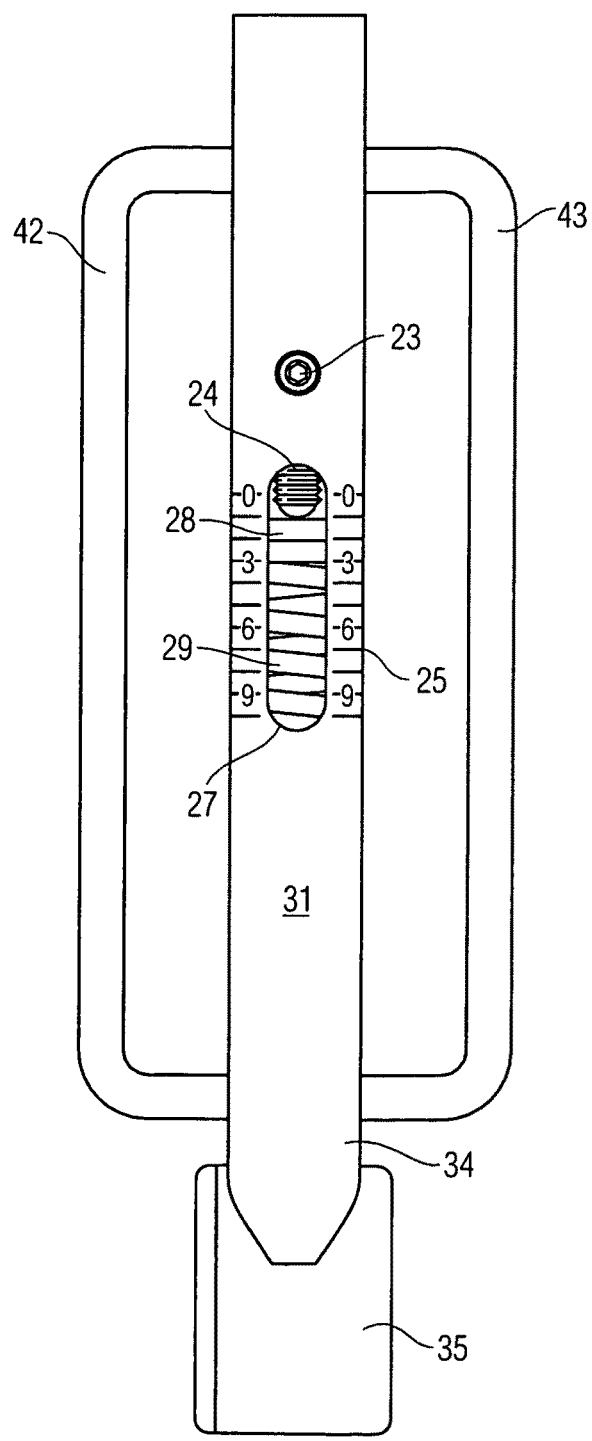
FIG. 14 is a plan view of the housing tube with slot therein showing the compression spring and scale.

With reference to FIGS. 1-3 and 12-14, a critical component of the device for treating hallux varus 10 is a tension mechanism assembly 20 which is comprised of a combination of components which are engineered to produce pressure on the toe in a graduated manner, to thereby cause a return of the toe to a normal configuration. There is shown a loading screw 24, loading nut 26, the spring spacer 28, compression spring 29 and chisel tip 30. These components fit into a housing tube 31. The components within the housing tube 31 are held in place by a set of loading nut set screws 32 which are screwed into tapped holes 33 in the loading nut 26. At a second end 34 of the housing tube 31, head for housing tube 35, main joint 36, plate cap 37, housing head standoff 38 and a plate cap screw 39. With reference to FIG. 2 there is supplied a screw driver 13 comprised of screw driver tip 14, an adjustment tool tee pin 15 and the adjustment tool body 16. The screw driver 13 is used to increase or decrease the tension mechanism by tightening or releasing the compression spring 29 by the use of the loading screw 24. The degree of tension is to be gauged by viewing the compression spring through slot 29 in juxtaposition with the number scale 25 (FIG. 14).

The tension mechanism assembly 20 is attached to the pivot mechanism 60. With the misdirected toe in the toe cradle 68 and with the tension mechanism assembly 20 assembled, there would not be pressure exerted on the toe. Tension is brought about by using screwdriver 13 on loading screw 24 on spring spacer 28 to tighten compression spring 29, forcing the chisel tip 30 against main joint 36 which through stem rod 22 and stem rod pivot adapter 64 forces pivot mechanism 60 against toe cradle 68 and in turn against the deviated toe. The pressure is viewed using the spring 29 in slot 27 in relationship to the scale 25 in FIG. 14.

At the start of therapy compression, spring 29 is at a low pressure setting (zero on scale) and as passive therapy continues more pressure is placed on the compression spring (numbers 6 and 9 on the scale) by the use of the screwdriver 13 turning loading screw 24 to force the chisel tip 30 against main joint 36 to transmit pressure on the pivot assembly and on to the deviated toe. In use, the pressure on the spring is gradually increased forcing the deviated toe into its normal position and would be seen through the relationship of the spring to numbers on scale 25. In FIG. 14 the hole 23 for receiving loading nut set screws 32 is shown. The slot 27 and scale 25 can be found on opposite sides of housing tube 31.

Foot Positioning Assembly

With reference to FIGS. 1-3, 8 and 12, there is attached to the housing tube 31 a closed end cuff wire 42 and 43, a bracket or pad clip 44 and a standard pad 46. The closed end cuff wire 42 and 43 aid in placing the straps of the foot positioning assembly so as to securely place the foot in the device as will be explained.

Referring to FIGS. 1, 2, 9, 10, 11 and 12 the foot positioning assembly 80 is comprised of a toe cuff 82 and a counterforce strap 84. With regard to FIGS. 9 and 10, the toe cuff 82 has a belt-like configuration and is comprised of a buckle 85 attached at its left end 86, and also a left portion 87 of Velcro, loop up followed to the right by an attached portion of Velcro, hook up 88 mounted on a velfoam fabric 92 followed by a weld tab 90.

Figure 11:
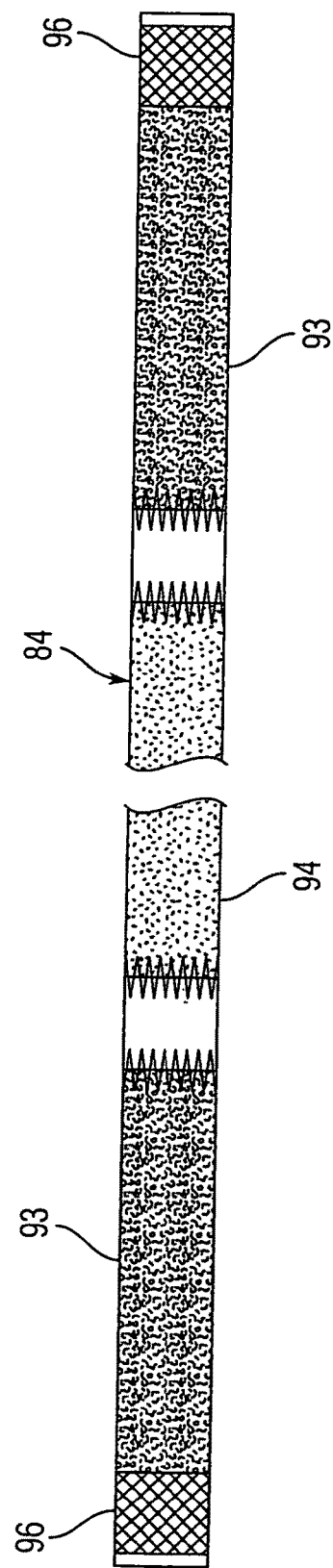
FIG. 11 is a top plan view of the counterforce strap.
Figure 12:
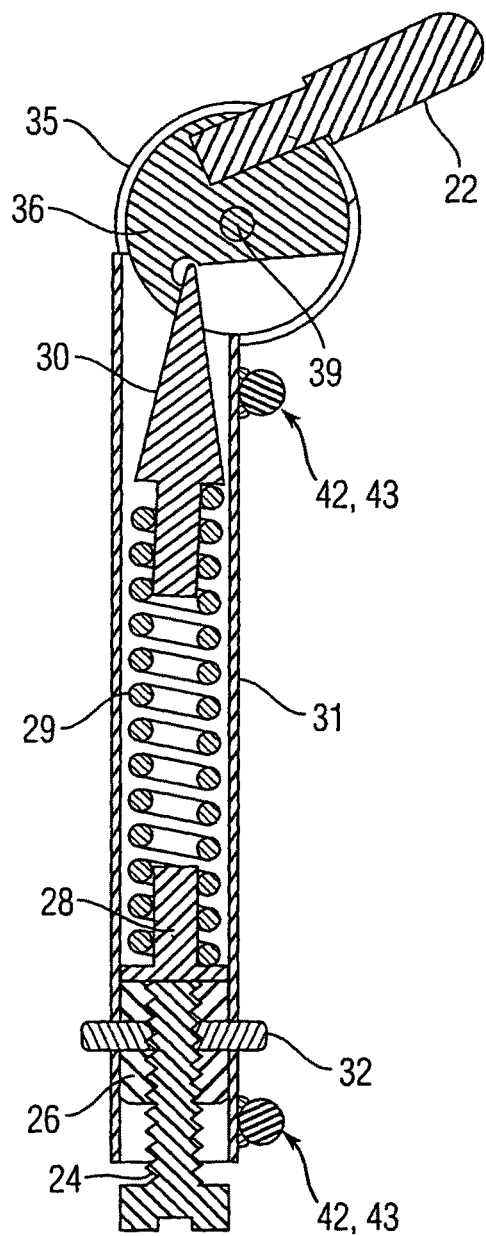
FIG. 12 is a cross-section view showing the assembled tension mechanism.

Referring to FIG. 11, the counterforce strap 84 has gripping tabs 96 at each end followed at each end by a short portion of Velcro hook up 93 in the middle between Velcro 93 is a much longer portion of Velcro loop up 94, all of which are mounted on velfoam fabric (not shown).

Method for Using the Device for Treating Hallux Varus

With reference to FIGS. 1-14; in the method for treating the misdirected toe, it is important to note that in order to produce a maximum therapeutic effect, it is essential that the foot and deformed toe be securely and fixedly placed in the device 10. This is accomplished by the use of belts, i.e., a toe cuff 82 and a counterforce strap 84 to secure the foot to the standard pad 46, and in the use of pivot mechanism 60.

With reference to FIGS. 1-3, 9-11 and 13, in order to set the foot into the Device for Treating Hallux Varus 10, toe cuff 82 and toe cuff buckle 85 are employed in conjunction with the closed end cuff wire top 42 and closed end cuff wire bottom 43. More specifically, with reference to FIGS. 1, 3, 9-11 and 13 the right end of toe cuff 82 is threaded through the closed end cuff wire top 42 and then through buckle 85. The toe cuff 82 is wrapped around the foot 81 (FIG. 13), and then the right end of toe cuff 82 is wound through the closed end cuff wire bottom 43 and tightened around the foot 81 and then attached by Velcro to toe cuff 82. It is important that the foot be firmly secured in the toe cuff 82.

With regard to FIGS. 1, 2, 8, 11 and 13, as added security to fixedly position the foot in the device 10 a counterforce strap 84 is employed adjacent to the toe cuff 82. In order to employ the counterforce strap 84 the left end is brought through the top left side of the closed end cuff wire and joined by left side Velcro 93 to center Velcro 94; the remainder of the counterforce strap is wrapped round the foot 81 and threaded through the left side of closed end cuff wire bottom 43 and secured attaching Velcro 93 at right side to Velcro at right side middle 94. It is important that counterforce strap 84 and toe cuff 82 tightly secure the foot in order that the tension mechanism effectively engages the toe positioned in the toe cradle 68. In FIG. 13, the arrow shows the direction tension is being applied to the toe.

Figure 3:
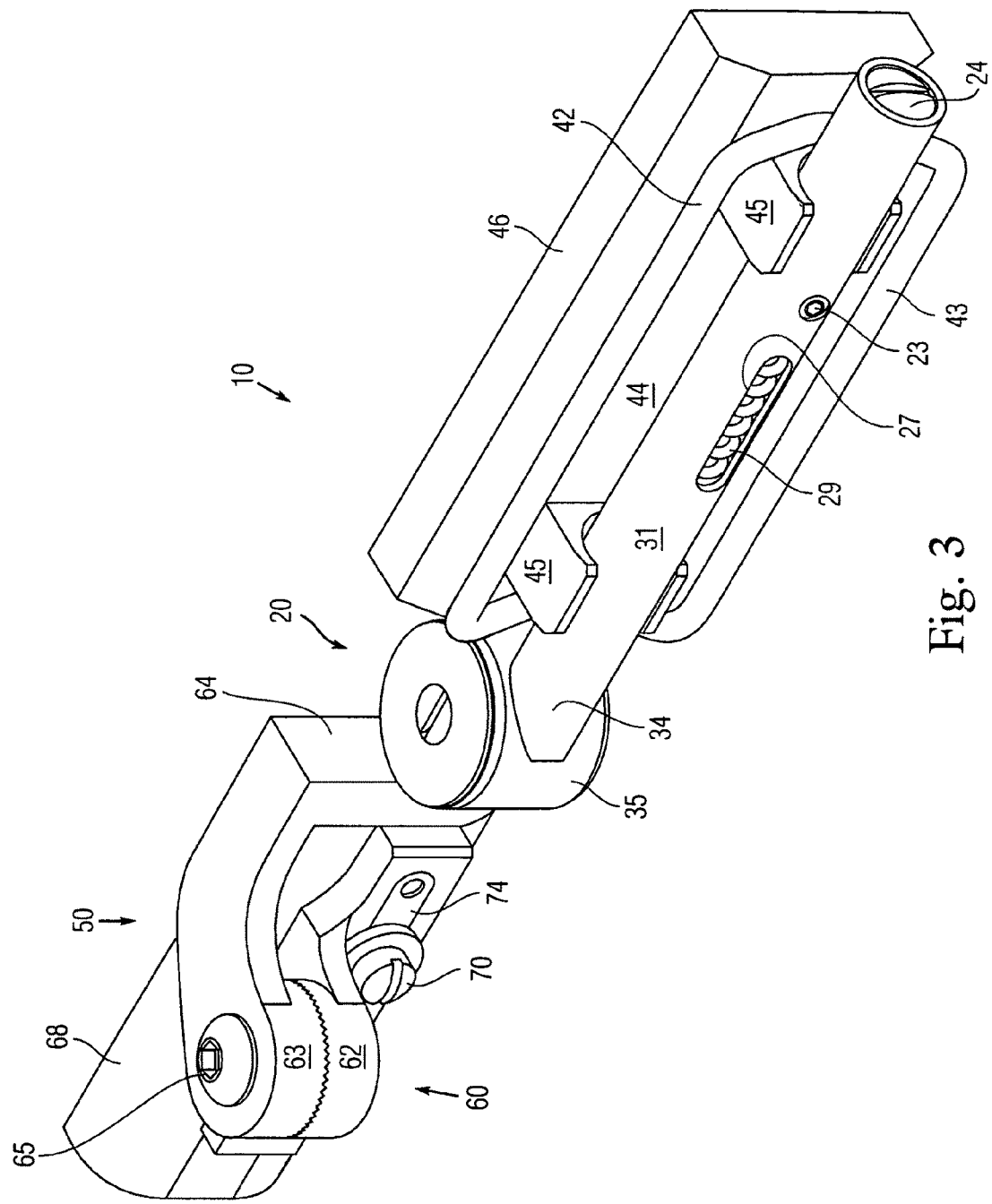
FIG. 3 is a top perspective view thereof without the strap assembly.
Figure 4:
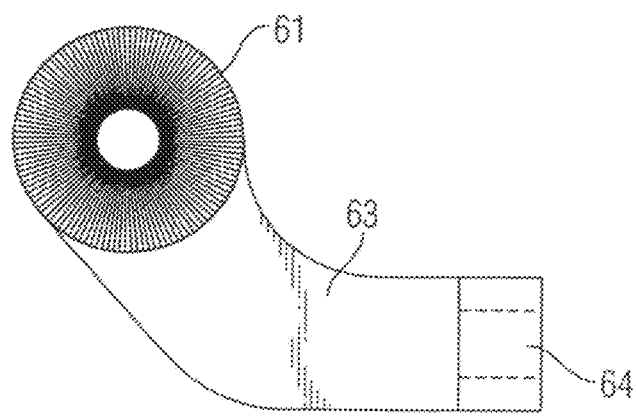
FIG. 4 is a bottom plan view of the toe cradle base pivot housing top member.
Figure 5:
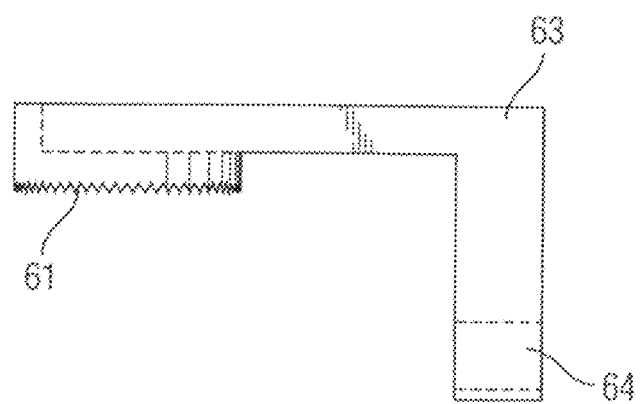
FIG. 5 is a side plan view thereof.
Figure 6:
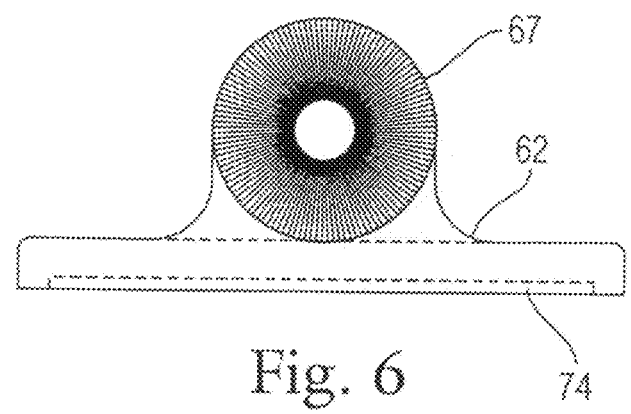
FIG. 6 is top plan view of the toe cradle base pivot housing bottom member.
Figure 7:
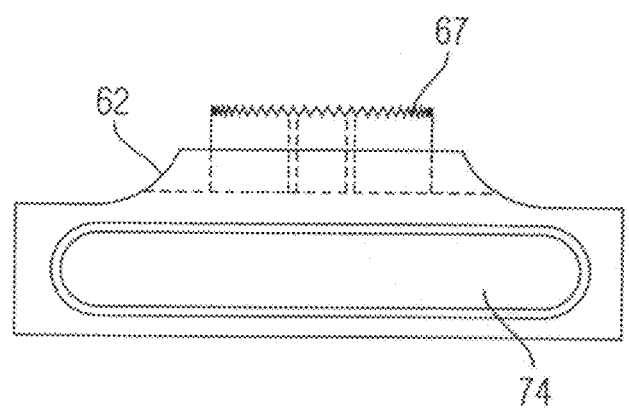
FIG. 7 is a front plan view thereof.
Figure 8:
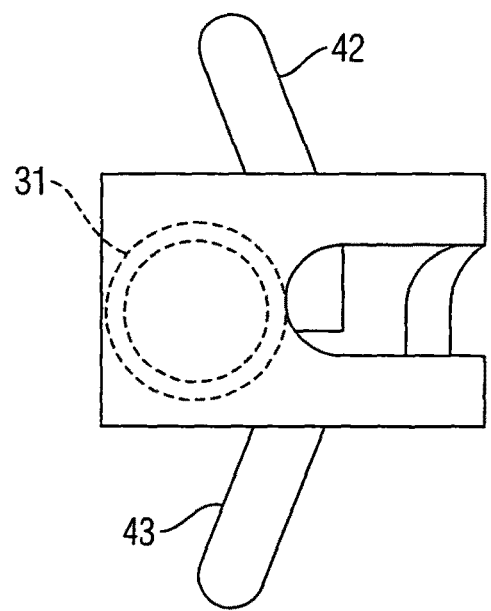
FIG. 8 is a right end plan view of the housing tube showing an end view of the closed end cuff wire.

With regard to FIGS. 1, 2 and 3, attached to the tension mechanism assembly 20 is a pad clip 44 which fixedly engages housing tube 31 through concave clips 45. Standard pad 46 has an adhering surface 48 which can be attached to the back 47 of pad clip 44 using adhesive, Velcro or a like holding means. This unitary arrangement allows the foot to be conveniently and firmly held in place by toe cuff 82 and counterforce strap 84. Also, in the housing tube 31 towards its center, there is a slot opening exposing compression spring 29. The slot opening will have a series of numbers by which the tension employed is to be indicated.

With regard to FIGS. 1-14, once the foot is secured, it is important that the misplaced toe 52 be brought into snug contact with toe cradle 68. This is accomplished by making adjustments with the pivot mechanism 60. Specifically, the toe cradle base pivot housing top member 63 is separated from the toe cradle base pivot housing bottom member 62 using pivot screw 65. Once the pivot mechanism 60 is separated, the toe cradle 68 which is joined to the bottom toe cradle base pivot housing 62 through slot 74 and toe cradle locking screw 70 attaching to toe cradle base 66, which in turn is attached to toe cradle 68, using toe cradle screw 69. Once the toe 52, toe cradle 68 and the bottom member toe cradle base pivot housing 62 have been placed, the toe cradle base pivot housing top member 63 is brought into position over the bottom member toe cradle base pivot housing 62. Stem rod 22 in the main joint 36 is inserted into the stem rod pivot adapter 64 found in the top member cradle base pivot housing 63 (FIGS. 2, 4, 5, 6 and 7). With the toe in the toe cradle, length is adjusted using slot 74 and toe cradle locking screw 70. With the spring 29 of the tension mechanism at its low reading, and the stem rod 22 inserted into the stem rod pivot adapter 64, the toe cradle base pivot housing top member 63 is joined to the bottom member 62 using pivot screw 65. Note that the teeth in the pivot housing (FIGS. 4-7) allow for angularity to be firmly fixed. It is important that the misdirected toe be firmly placed in the toe cradle using the pivot mechanism; that the tension mechanism be set at zero or low tension to be joined to the pivot mechanism; and that the foot be secure in the device. Once these conditions are met, tension can be placed on the misdirected toe using screw driver 13 and loading screw 24. The pressure can be viewed using compression spring 29 and scale 25 (FIG. 14).

Described in another way, the invention may be described as being a device for treating Hallux Varus and for straightening a toe which has deviated away from the midline of the foot comprising a tension mechanism, an assembly for retaining the toe in contact with said tension mechanism and an assembly for securely positioning the foot in said device, such that when pressure is applied to the toe using the tension mechanism, the toe can be returned to its normal position. In the device the tension mechanism is one which is able to produce a graded amount of tension, and employs a compression spring to force a chisel tip against a main joint; and further the assembly for retaining the toe in contact with the tension mechanism comprises a pivot mechanism having top and bottom teeth employed to firmly fix angularity and to bring the toe cradle securely against the deviated toe.

As a specific feature, the top and bottom of the device are mirror images of each other allowing the device to treat either the right or left toe.

An important feature of the invention is an assembly for retaining the toe which is joined to the tension mechanism employing a stem rod in the main joint which is inserted into stem rod pivot adapter.

The invention also includes a method for treating Hallux Varus comprising securely positioning the foot in the device for treating Hallux Varus, positioning the deviated tow in a toe cradle and applying pressure to the toe employing a mechanism having a compression spring used to force a chisel tip against a main joint.

In the device for treating Hallux Varus, the means for securing the foot to the device is a series of straps; the means for positioning the deviated toe is a toe cradle and pivot mechanism; the means for applying graded pressure comprises a compression spring and a chisel tip applied against a main joint; and the means for coupling the means for positioning the deviated toe to the means for applying graded pressure to the toe is a stem rod attached to the main joint which is to be inserted into the stem rod pivot adapter.

Protocol of Use

The inventive device is to be used as follows.

Where there has been surgical intervention to correct the misdirected toe, the device for treating Hallux Varus is to be used three (3) times a day starting out at ten (10) minute intervals, working up to three (3) hours a day. Tension starts at what the patient can tolerate.

No major pain is to be experienced using the device of this invention. The initial setting using the device should be pain-free. Time of use is more important than the application of tension.

In general, tension is to be increased every five (5) days by one full turn provided that post wear discomfort is less than 30 minutes. In the event that post wear discomfort is greater than 30 minutes, decrease tension and contact the doctor for advice.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A device for treating Hallux Varus and for straightening a toe which has deviated away from a midline of a foot, comprising:
 a tension mechanism;
 an assembly for retaining the toe in contact with the device; and
 an assembly for securely positioning the foot in said device, such that when a pressure is applied to the toe using the tension mechanism, the toe is capable of returning to a normal position,
 wherein the tension mechanism comprises a main joint, a chisel tip, and a compression spring configured to force the chisel tip against the main joint for producing a graded amount of tension.

2. The device of claim 1, wherein the assembly for retaining the toe comprises a toe cradle and a pivot mechanism having top and bottom teeth and is configured to firmly fix angularity and to bring the toe cradle securely against the deviated toe.

3. The device of claim 1, wherein top and bottom of the device are mirror images of each other allowing the device to treat either the right or left toe.

4. The device of claim 1, wherein
 the tension mechanism further comprises a stem rod in the main joint, and
 the pivot mechanism comprises a stem rod pivot adapter engageable with the stem rod to join the tension mechanism with the assembly for retaining the toe.

5. The device of claim 1, wherein the tension mechanism is configured to apply the pressure which is a graded pressure providable by the compression spring.

6. The device of claim 5, wherein the tension mechanism further comprises:
 a housing tube housing the compression spring;
 a spring spacer in the compression spring; and
 a loading screw configured to push the spring spacer so as to gradually tighten the compression spring to provide the graded pressure.

7. The device of claim 1, wherein the assembly for securely positioning the foot in said device comprises a series of straps.

8. A method of treating Hallux Varus comprising:
 securely positioning a foot in a device for treating Hallux Varus,
 positioning a deviated toe of the foot in a toe cradle, and
 applying a pressure to the toe by employing a mechanism having a main joint, a chisel tip, and a compression spring,
 wherein the compression spring is employed to force the chisel tip against the main joint.

9. The method of claim 8, wherein the foot is securely positioned in the device by a positioning assembly,
 wherein
 the positioning assembly includes a toe cradle and a pivot mechanism having top and bottom teeth, and
 the positioning assembly firmly fixes angularity and brings the toe cradle securely against the deviated toe.

10. The method of claim 9, wherein
 the mechanism that applies the pressure further comprises a stem rod in the main joint, and
 the device further comprises a stem rod pivot adapter which engages with the stem rod to join the mechanism with the positioning assembly.

11. The method of claim 10, wherein the mechanism that applies the pressure further comprises:
 a housing tube housing the compression spring;
 a spring spacer in the compression spring; and
 a loading screw,
 wherein said applying the pressure to the toe comprises:
  applying a force on the loading screw and the spring spacer to gradually tighten the compression spring, causing the chisel tip against the main joint to force the pivot mechanism, through the stem rod and the stem rod pivot adapter, against the toe cradle and in turn against the deviated toe.

12. The method of claim 9, wherein the positioning assembly comprises a series of straps to securely position the foot in said device.

13. The method of claim 8, wherein top and bottom of the device are mirror images of each other and allow the device to treat either the right or left toe.

14. The method of claim 8, wherein the pressure applied to the toe is a graded pressure provided by the compression spring.

15. A device for treating Hallux Varus comprising:
- means for securing a foot to the device;
- means for positioning a deviated toe of the foot in contact with the device;
- means for applying a graded pressure to the deviated toe; and
- means for coupling the means for positioning the deviated toe to the means for applying the graded pressure to the toe which is configured to aid in returning the deviated toe to its normal position, wherein
- the means for positioning the deviated toe is a toe cradle and a pivot mechanism, and
- the means for applying the graded pressure comprises a compression spring, a main joint, and a chisel tip configured to be applied against the main joint.

16. The device of claim 15, wherein the means for securing the foot to the device is a series of straps.

17. The device of claim 15, wherein
- the pivot mechanism includes a stem rod pivot adapter, and
- the means for coupling the means for positioning the deviated toe to the means for applying the graded pressure to the toe is a stem rod attached to the main joint which is to be inserted into the stem rod pivot adapter.

18. The device of claim 15, wherein the pivot mechanism includes top and bottom teeth and is configured to firmly fix angularity and to bring the toe cradle securely against the deviated toe.

19. The device of claim 15, wherein top and bottom of the device are mirror images of each other allowing the device to treat either the right or left toe.

20. The device of claim 15, wherein the means for applying the graded pressure further comprises:
- a housing tube housing the compression spring;
- a spring spacer in the compression spring; and
- a loading screw configured to push the spring spacer so as to gradually tighten the compression spring to provide the graded pressure.

\* \* \* \* \*